(12) United States Patent
Nesterenko et al.

(10) Patent No.: US 9,067,199 B2
(45) Date of Patent: *Jun. 30, 2015

(54) METHOD FOR MAKING A CATALYST COMPRISING A PHOSPHORUS MODIFIED ZEOLITE TO BE USED IN AN ALCOHOLS DEHYDRATION PROCESS

(75) Inventors: Nikolai Nesterenko, Nivelles (BE); Sander Van Donk, Sainte-Adresse (FR); Delphine Minoux, Nivelles (BE); Jean-Pierre Dath, Beloeil (BE)

(73) Assignee: TOTAL RESEARCH & TECHNOLOGY FELUY, Seneffe (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/522,633

(22) PCT Filed: Jan. 25, 2011

(86) PCT No.: PCT/EP2011/050964
§ 371 (c)(1),
(2), (4) Date: Sep. 28, 2012

(87) PCT Pub. No.: WO2011/089263
PCT Pub. Date: Jul. 28, 2011

(65) Prior Publication Data
US 2013/0197291 A1 Aug. 1, 2013

(30) Foreign Application Priority Data
Jan. 25, 2010 (EP) ..................... 10151507

(51) Int. Cl.
*C07C 1/24* (2006.01)
*B01J 29/85* (2006.01)
*B01J 29/06* (2006.01)
*B01J 29/40* (2006.01)
*B01J 37/28* (2006.01)
*C07C 1/20* (2006.01)
*B01J 27/16* (2006.01)
*B01J 37/00* (2006.01)

(52) U.S. Cl.
CPC . *B01J 29/85* (2013.01); *B01J 27/16* (2013.01); *B01J 29/06* (2013.01); *B01J 29/40* (2013.01); *B01J 37/0009* (2013.01); *B01J 37/0045* (2013.01); *B01J 37/28* (2013.01); *B01J 2229/18* (2013.01); *B01J 2229/36* (2013.01); *B01J 2229/37* (2013.01); *B01J 2229/42* (2013.01); *C07C 1/20* (2013.01); *C07C 2529/40* (2013.01); *C07C 1/24* (2013.01)

(58) Field of Classification Search
CPC .................. B01J 29/40; B01J 29/005
USPC ........ 585/639, 640, 641, 642; 502/60, 65, 77, 502/121, 150, 155, 162, 208
See application file for complete search history.

(56) References Cited

U.S. PATENT DOCUMENTS

| | | | |
|---|---|---|---|
| 4,356,338 A | 10/1982 | Young | |
| 4,433,189 A * | 2/1984 | Young | 585/640 |
| 5,171,921 A * | 12/1992 | Gaffney et al. | 585/653 |
| 5,231,064 A | 7/1993 | Absil et al. | |
| 5,367,100 A * | 11/1994 | Gongwei et al. | 585/640 |
| 5,573,990 A | 11/1996 | Wang et al. | |
| 7,230,151 B2 | 6/2007 | Martens et al. | |
| 2003/0078463 A1* | 4/2003 | Martens et al. | 585/639 |
| 2005/0137080 A1* | 6/2005 | Chang et al. | 585/639 |
| 2006/0106270 A1 | 5/2006 | Glover et al. | |
| 2007/0149384 A1* | 6/2007 | Ghosh et al. | 502/60 |
| 2011/0098518 A1 | 4/2011 | Minoux et al. | |
| 2011/0105815 A1 | 5/2011 | Minoux et al. | |
| 2011/0124939 A1 | 5/2011 | Minoux et al. | |
| 2011/0137096 A1 | 6/2011 | Minoux et al. | |

FOREIGN PATENT DOCUMENTS

| | | |
|---|---|---|
| EP | 2082802 A1 | 7/2009 |
| EP | 2143700 A1 | 1/2010 |
| WO | 2009098262 A1 | 8/2009 |

OTHER PUBLICATIONS

Ouyang et al. Catalytic Conversion of Bio-Ethanol to Ethylene over La-Modified HZSM-5 Catalysts in a Bioreactor. Catal Lett (2009) 132:64-74.*
Office Action issued in Japanese Patent Application No. 2012-549378, dated Oct. 25, 2013 (3 pages).
Office Action issued in European Patent Application No. 11701105.6-1454, dated Apr. 7, 2014 (5 pages).
Office Action issued in Japanese Patent Application No. 2012-549378, dated Aug. 5, 2014 and English translation thereof (5 pages).
Iwanami Rikagakujiten vol. 5, edited by Iwanami, Apr. 24, 1998, 2nd edition, p. 1497.

* cited by examiner

*Primary Examiner* — In Suk Bullock
*Assistant Examiner* — Sharon Pregler

(57) ABSTRACT

The present invention is the use of a catalyst to convert an alcohol into light olefins in a dehydration process wherein said catalyst comprises a phosphorus modified zeolite and is made by a method comprising the following steps in this order, a) the essential portion of the phosphorus is introduced into a zeolite comprising at least one ten members ring in the structure,
b) the phosphorus modified zeolite of step a) is mixed with at least a component selected among one or more binders, salts of alkali-earth metals, salts of rare-earth metals, clays and shaping additives,
b)* making a catalyst body from mixture b),
c) an optional drying step or an optional drying step followed by a washing step,
d) a calcination step,
d*) an optional washing step followed by drying,
e) optionally a small portion of phosphorus is introduced in the course of step b) or b)* or at end of step b) or b)*.

20 Claims, 1 Drawing Sheet

METHOD FOR MAKING A CATALYST COMPRISING A PHOSPHORUS MODIFIED ZEOLITE TO BE USED IN AN ALCOHOLS DEHYDRATION PROCESS

CROSS-REFERENCE TO RELATED APPLICATIONS

This application claims the benefit of PCT/EP2011/050964, filed Feb. 25, 2011, which claims priority from EP 10151507.0, filed Jan. 25, 2010.

FIELD OF THE INVENTION

The present invention relates to a method for making a catalyst comprising a phosphorus modified zeolite to be used to convert an alcohol into light olefins in a dehydration process to convert at least an alcohol into the corresponding olefin wherein said catalyst comprises a phosphorus modified zeolite. Olefins are traditionally produced from petroleum feedstocks by catalytic or steam cracking processes. These cracking processes, especially steam cracking, produce light olefin(s), such as ethylene and/or propylene, from a variety of hydrocarbon feedstock. Ethylene and propylene are important commodity petrochemicals useful in a variety of processes for making plastics and other chemical compounds.

The limited supply and increasing cost of crude oil has prompted the search for alternative processes for producing hydrocarbon products.

Olefins can be produced by dehydration of the corresponding alcohol. Ethanol, as well as higher alcohols such as propanol, butanol can be obtained by fermentation of carbohydrates. Made up of organic matter from living organisms, biomass is the world's leading renewable energy source. Recently, new routes to produce ethanol and higher alcohols from syngas have been described.

BACKGROUND OF THE INVENTION

Catalysts comprising a phosphorus modified zeolite (the phosphorus modified zeolite is also referred as P-zeolite) are known. The following prior arts have described various methods to make said catalysts.

US 2006 106270 relates to the use of a dual-function catalyst system in the hydrocarbon synthesis reaction zone of an oxygenate to propylene (OTP) process that operates at relatively high temperatures preferably with a steam diluent and uses moving bed reactor technology. The dual-functional catalyst system comprises a molecular sieve having dual-function capability dispersed in a phosphorus-modified alumina matrix containing labile phosphorus and/or aluminum anions. It is explained that the hydrothermal stabilization effect that is observed when this phosphorus-modified alumina matrix is utilized is caused by migration or dispersion of phosphorus and/or aluminum anions from this matrix into the bound molecular sieve. These anions are then available to repair, anneal and/or stabilize the framework of the molecular sieve against the well-known dealumination mechanism of molecular sieve framework destruction or modification that is induced by exposure to steam at temperatures corresponding to those used in the OTP reaction zone and in the regeneration zone.

U.S. Pat. No. 4,356,338 discloses a method for decreasing catalyst coking and extending the usable catalyst life by pre-treatment of the catalyst with steam and/or a phosphorus-containing compound. Pretreatment may be accomplished by the impregnation of the catalyst or of the catalyst/binder in combination with a phosphorus containing compound to deposit approximately 4 wt. % of phosphorus thereon, and preferably from about 2% to about 15% by weight of phosphorus, based on the weight of the catalyst or catalyst/binder matrix being treated.

U.S. Pat. No. 5,231,064 is directed to a fluid catalyst comprising clay and a zeolite, at least one of which has been treated with a phosphorus containing compound, for example ammonium dihydrogen phosphate or phosphoric acid, and which is spray dried at a low pH, preferably lower than about 3. Said catalysts are deemed to advantageously exhibit reduced attrition.

EP 511013 A2 provides an improved process for the production of C2-C5 olefins from higher olefinic or paraffinic or mixed olefin and paraffin feedstocks. In accordance with this prior art, the hydrocarbon feed materials are contacted with a particular ZSM-5 catalyst at elevated temperatures, high space velocity and low hydrocarbon partial pressure to produce lower olefins. The catalysts is treated with steam prior to use in the hydrocarbon conversion. The active catalyst component is phosphorus-containing ZSM-5 having a surface Si/Al ratio in the range 20-60. Preferably, the phosphorus is added to the formed ZSM-5 as by impregnating the ZSM-5 with a phosphorus compound in accordance with the procedures described, for example, in U.S. Pat. No. 3,972,832. Less preferably, the phosphorus compound can be added to the multicomponent mixture from which the catalyst is formed. The phosphorus compound is added in amount sufficient to provide a final ZSM-5 composition having 0.1-10 wt. % phosphorus, preferably 1-3 wt. %.

The phosphorus-containing ZSM-5 is preferably combined with known binders or matrices such as silica, kaolin, calcium bentonite, alumina, silica aluminate and the like. The ZSM-5 generally comprises 1-50 wt. % of the catalyst composition, preferably 5-30 wt. % and most preferably 10-25 wt. %.

EP 568913 A2 describes a method for preparing a ZSM-5 based catalyst adapted to be used in the catalytic conversion of methanol or dimethyl ether to light olefins, wherein it comprises the following consecutive steps:
  mixing a zeolite ZSM-5 based catalyst with silica sol and ammonium nitrate solution,
  kneading, moulding, drying and calcining the mixture,
  exchanging the modified zeolite with a solution of HCl at 70-90° C.,
  drying and calcining the H-modified zeolite,
  impregnating the H-modified zeolite with phosphoric acid under reduced pressure,
  drying and calcining the P-modified zeolite,
  impregnating the P-modified zeolite with a solution of rare earth elements under reduced pressure,
  drying and calcining the P-rare earths-modified zeolite,
  hydrothermally treating the P-rare earths-modified zeolite at 500-600° C. with water vapour, and
  calcining the modified zeolite.

WO 03 020667 relates to a process of making olefin, particularly ethylene and propylene, from an oxygenate feed, comprising contacting an oxygenate feed with at least two different zeolite catalysts to form an olefin composition, wherein a first of the zeolite catalysts contains a ZSM-5 molecular sieve and a second of the zeolite catalysts contains a zeolite molecular sieve selected from the group consisting of ZSM-22, ZSM-23, ZSM-35, ZSM-48, and mixtures thereof. The ZSM-5 can be unmodified, phosphorous modified, steam modified having a micropore is volume reduced to not less than 50% of that of the unsteamed ZSM-5, or various mixtures thereof. According to one embodiment, the zeolite is modified with a phosphorous containing compound to control reduction in pore volume. Alternatively, the zeolite is steamed, and the phosphorous compound is added prior to or after steaming. The amount of phosphorous, as measured on an elemental basis, is from 0.05 wt. % to 20 wt. %, and preferably is from 1 wt. % to 10 wt. %, based on the weight of the zeolite molecular sieve. Preferably, the atomic ratio of phosphorus to framework aluminum (i.e. in the zeolite framework) is not greater than 4:1 and more preferably from 2:1 to 4:1. Incorporation of a phosphorus modifier into the catalyst of the invention is accomplished, according to one embodiment, by contacting the zeolite molecular sieve either alone or the zeolite in combination with a binder with a solution of an appropriate phosphorus compound. The solid zeolite or zeolite catalyst is separated from the phosphorous solution, dried and calcined. In some cases, the added phosphorous is converted to its oxide form under such conditions. Contact with the phosphorus-containing compound is generally conducted at a temperature from 25° C. to 125° C. for a time from 15 minutes to 20 hours. The concentration of the phosphorus in the zeolite may be from 0.01 wt. % to 30 wt. %. This prior art discloses a non-formulated P-ZSM-5.

A common way to produce a formulated P-zeolite containing catalyst consists in the impregnation of the already preformulated zeolite (e.g. the zeolite+ a binder) with P-compounds or phosphorous addition to the reaction medium.

A great number of patents disclose the recipe for preparation of the active phase (non-formulated phosphated zeolite) by means of zeolite phosphatation and their use in methanol conversion. Some of these references contain the options of further blending the active phase with binder. However, the active phase is good as such in the reaction. It is assumed that the binder plays only the role of diluent what is not normally the case. The process of the present invention differs from a great number of known in the art preparation of the P-zeolite based active phase due to referring to preparation of formulated catalyst and implementation of the phosphatation step at the first stage. Moreover the phosphatation of the zeolite (formation of the active phase) at the first step does not necessarily leads to a suitable catalyst. On the contrary, the overall recipe results in a good catalyst.

The catalyst referred to in the present invention comprises a zeolite and at least a component selected among one or more binders, salts of alkali-earth metals, salts of rare-earth metals, clays and shaping additives. The metal salts, binder and clays may also adsorb the phosphorous interfering and even competing with zeolite preventing a proper zeolite phosphatation. The presence of traces of metals adsorbing preferentially phosphorous could even more perturb the zeolite phophatation. This often leads to non-selective catalysts due to poor reproducibility and binder pore plugging. The method of the present invention provides a solution to selectively phosphatize zeolite overcoming the side effects of binder, metal salts or clays presence. Thus, the invention discloses that the preparation of the catalyst requires the phosphatation of zeolite before introducing any other components such as binder, metals, clays and shaping additives. This method insures the reproducibility of the preparation, the hydrothermal stability and the good catalyst performance.

BRIEF DESCRIPTION OF THE INVENTION

The present invention relates to the use of a catalyst to convert at least an alcohol into light olefins in a dehydration process wherein said catalyst comprises a phosphorus modified zeolite and is made by a method comprising the following steps in this order, a) the essential portion of the phosphorus is introduced into a zeolite comprising at least one ten members ring in the structure,
b) the phosphorus modified zeolite of step a) is mixed with at least a component selected among one or more binders, salts of alkali-earth metals, salts of rare-earth metals, clays and shaping additives,
b)* making a catalyst body from mixture b),
c) an optional drying step or an optional drying step followed by a washing step,
d) a calcination step,
d*) an optional washing step followed by drying,
e) optionally a small portion of phosphorus is introduced in the course of step b) or b)* or at end of step b) or b)*.

Advantageously the zeolite (or molecular sieve) contains less that 1000 wppm of sodium, less that 1000 wppm of potassium and less that 1000 wppm of iron.

Advantageously the zeolite contains less than 200 ppm of alkali and alkali-earth metals.

Advantageously the bulk Si/Al ratio of initial zeolite is below 20. Advantageously the zeolite contains less than 100 ppm of red-ox and noble elements such as Zn, Cr, Ti, Rh, Mn, Ni, V, Mo, Co, Cu, Cd, Pt, Pd, Ir, Ru, Re.

The phosphorus source is advantageously substantially free of metal compounds. It is advantageously selected among $H_3PO_4$, ammonium phosphates or organic P-compounds.

In an embodiment the phosphorus of step e) can be introduced as a component of the binder or of the clays.

The amount of phosphorous introduced into the zeolite at step a) can be from 0.5 to 30 wt %, but preferably from 0.5 to 9%.

Advantageously the molar P/Al ratio at step a) is higher than 1 by providing the excess of phosphatation agent.

The formulation steps b) and c) can be performed by means of spray—drying, extrusion, oil drop etc.

In accordance with the present invention, at the step c) and d*) the catalyst is treated with water for a period of time advantageously from 0.5 to 48 hours, preferably for a period of time from about 1 to 36 hours and most preferably from about 2 to 24 hours. The water is at a temperature between about 10° and 180° C., preferably between about 15° and 100° C. and most preferably between about 20° and 60° C. Following the water treatment, the catalyst is dried at about 60-350° C. Optionally, the water can contain ammonium or/and at least one of the ions selected from the group consisting of Li, Ag, Mg, Ca, Sr, Ba, Ce, Al, La, and mixtures thereof.

At end of step a) it is not mandatory to separate the P-zeolite from the reaction medium, the binders, salts of alkali-earth metals, salts of rare-earth metals, clays and shaping additives can be added directly into the reaction medium.

In a preferred embodiment, a low sodium content binder and clays are used.

Before the phosphatation of step a) the zeolite can be subjected to various treatments including, ion exchange, steaming, acid treatment, surface passivating by silica deposition etc.

In a preferred embodiment the sodium content in the binder and the clays is less that 5000 ppm of sodium.

Preferred zeolite structures are selected from the MFI, MTT, FER, MEL, TON, MWW, EUO, MFS, ZSM-48.

DETAILED DESCRIPTION OF THE INVENTION

Figure 1:
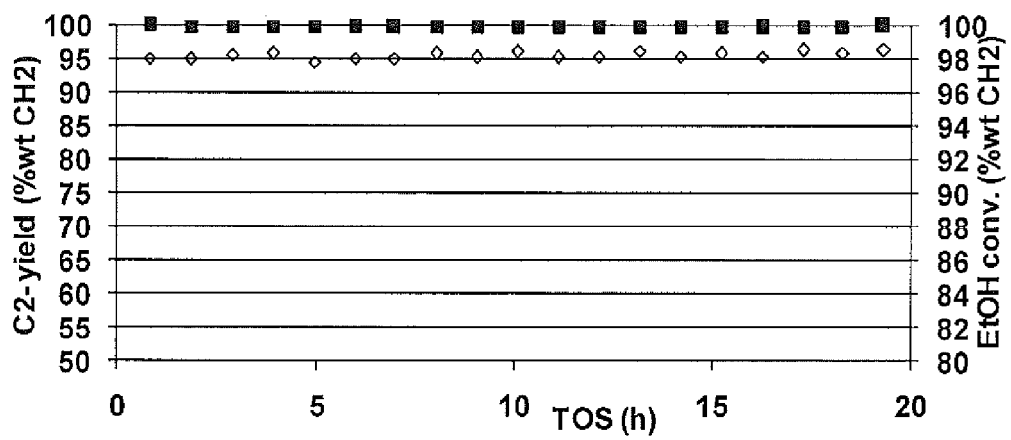
FIG. 1 shows the evolution of the ethanol conversion (full rectangles) and the ethylene yield (open lozenges) as a function of time of stream. Catalyst A. Surfin 96 bio-ethanol—400° C.–2bara—WHSV(Ethanol): 7 h-1

As regards the dehydration process to convert an alcohol into an olefin, this process has been described in a lot of patent applications. One can cite WO/2009/098262, WO/2009/098267, WO/2009/098268 and WO 2009/098269, the content of which is incorporated in the present application.

The alcohol is any alcohol provided it can be dehydrated to the corresponding olefin. By way of example mention may be made of alcohols having from 2 to 10 carbon atoms. Advantageously the invention is of interest for ethanol, propanol, butanol and phenylethanol.

As regards the zeolite containing at least one 10 members ring into the structure, one can cite the crystalline silicates. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, oxygen and optionally boron.

The three-letter designations "MFI" and "MEL" each representing a particular crystalline silicate structure type as established by the Structure Commission of the International Zeolite Association. Examples of a crystalline silicate of the MFI type are the synthetic zeolite ZSM-5 and silicalite and other MFI type crystalline silicates known in the art. Examples of a crystalline silicate of the MEL family are the zeolite ZSM-11 and other MEL type crystalline silicates known in the art. Other examples are Boralite D and silicalite-2 as described by the International Zeolite Association (Atlas of zeolite structure types, 1987, Butterworths). The preferred crystalline silicates have pores or channels defined by ten oxygen rings.

Crystalline silicates are microporous crystalline inorganic polymers based on a framework of $XO_4$ tetrahedra linked to each other by sharing of oxygen ions, where X may be trivalent (e.g. Al, B, ...) or tetravalent (e.g. Ge, Si, ...). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bidirectional intersecting pore system with the following pore diameters: a straight channel along [010]: 0.53-0.56 nm and a sinusoidal channel along [100]:0.51-0.55 nm. Crystalline silicates with the MEL structure possess a bidirectional intersecting straight pore system with straight channels along [100] having pore diameters of 0.53-0.54 nm.

In a specific embodiment the crystalline silicate is steamed to remove aluminium from the crystalline silicate framework before phosphatation. The steam treatment is conducted at elevated temperature, preferably in the range of from 425 to 870° C., more preferably in the range of from 540 to 815° C. and at pressure 1-5 bara and at a water partial pressure of from 13 to 200 kPa. Preferably, the steam treatment is conducted in an atmosphere comprising from 5 to 100% steam. The steam atmosphere preferably contains from 5 to 100 vol % steam with from 0 to 95 vol % of an inert gas, preferably nitrogen. A more preferred atmosphere comprises 72 vol % steam and 28 vol % nitrogen i.e. 72 kPa steam at a pressure of one atmosphere. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

Additionally, if during the preparation of the zeolite to be phosphatized alkaline or alkaline earth metals have been used, the molecular sieve might be subjected to an ion-exchange step. Conventionally, ion-exchange is done in aqueous solutions using ammonium salts or inorganic acids.

As regards the introduction of P into the zeolite, by way of example said P-modified zeolite is made by a process comprising in that order:
introducing P;
separation of the solid from the liquid if any;
an optional washing step or an optional drying step or an optional drying step followed by a washing step;
a calcination step;

Optionally, the contact with the phosphorus-containing compound is conducted at a temperature from 40° C. to 110°. P can be introduced by any means or, by way of example, according to the recipe described in U.S. Pat. No. 3,911,041.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

According to a specific embodiment the phosphorous modified zeolite is made by a process comprising in that order:
selecting a zeolite;
steaming at a temperature ranging from 400 to 870° C. for 0.01-200 h;
optional leaching with an aqueous acid solution at conditions effective to remove a substantial part of Al from the zeolite;
introducing P with an aqueous solution containing the source of P at conditions effective to introduce advantageously at least 0.05 wt % of P;
separation of the solid from the liquid;
an optional washing step or an optional drying step or an optional drying step followed by a washing step;
an optional calcination step.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen.

The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

As regards step b), and the binder, it is selected so as to be resistant to the temperature and other conditions employed in the processes using the catalyst. The binder is an inorganic material selected from silica, metal silicates, metal oxides such as $ZrO_2$ and/or metals, or gels including mixtures of silica and metal oxides. It is desirable to provide a catalyst having a good crush strength. This is because in commercial use, it is desirable to prevent the catalyst from breaking down into powder-like materials. Such oxide binders have been employed normally only for the purpose of improving the crush strength of the catalyst. A particularly preferred binder for the catalyst of the present invention comprises silica. The relative proportions of the finely divided crystalline silicate material and the inorganic oxide matrix of the binder can vary widely.

As regards step b)*, in addition to enhancing the catalyst strength properties, the matrix material allows the molecular sieve crystallite powder to be bound into larger particle sizes suitable for commercial catalytic processes. The formulation of the mixture b) may be formed into a wide variety of shapes including extrudates, spheres, pills, and the like. The binder material is often, to some extent, porous in nature and may or may not be effective to promote the desired conversion of methanol to light olefins. The matrix material may also promote conversion of the feed stream and often provides reduced selectivity to the desired product or products relative to the catalyst.

Types of silica sols used to form a bound catalyst for use in alcohol dehydration process are commercially available as aquasols or organosols containing dispersed colloidal silica particles. For example, sodium silicate can be used as a silica sol. Otherwise, a silica gel, fumed or pyrogenic silica may also be used to provide a silica binder in the molecular sieve catalyst. Silicic acid is another possible source of silica. If a magnesia binder is desired, the starting slurry will contain hydrolyzed magnesium alkoxide. When a zirconia binder is used for the catalyst preparation, the preferred starting acidic sol is an aqueous zirconium acetate solution, which is preferably combined with a urea gelling agent. Advantageously, the binder contains low amount of sodium below 1000 ppm.

As regards to the clays, It is preferred to optionally add a clay to the catalyst. The clay is usually added to the catalyst slurry before the mixing of the molecular sieve and binder, and the resultant slurry is mixed and spray dried. Clays that are used in this process to form a hardened product include, but are not limited to, kaolin, kaolinite, montmorillonite, saponite, bentonite, attapulgite and halloysite. Clays contribute to strength as a binder enhancing the attrition resistance properties of the catalyst particles, and clays in combination with binders contribute to the hardness of the particles. Clays also start as small particles and have a higher density, such that when combined with the molecular sieve and binder provide for denser particles, imparting the desirable characteristic of higher density.

As regards the salts of alkali-earth metals, salts of rare-earth metals, the metals are advantageously Ca, Mg, Sr, Ce, La or a combination thereof.

As regards the proportions of the P-zeolite, the one or more binders, salts of alkali-earth metals, salts of rare-earth metals, clays and shaping additives, advantageously the proportion of the P-zeolite is from 5 to 95 w % of the catalyst. The catalyst comprises the P-zeolite and at least a component selected among one or more binders, salts of alkali-earth metals, salts of rare-earth metals, clays and shaping additives. The amount of P-modified zeolite which is contained in the catalyst ranges more advantageously from 15 to 90 weight percent of the total catalyst, preferably 20 to 70 weight percent of the catalyst. When adding clay, the clay forms between about 10 and about 80 wt-% of the dried catalyst product. The concentration of the salts of alkali-earth metals and salts of rare-earth metals can be from 0.1 to 15 wt % of the catalyst on metal basis (Me). Advantageously the molar ratio of (Al+Me)/P in the catalyst is in the range 0.5 to 3, where the Me is alkali or rare-earth.

In mixing the P-zeolite with at least a component selected among one or more binders, salts of alkali-earth metals, salts of rare-earth metals and clays, the catalyst may be formulated into pellets, extruded into other shapes, or formed into spheres or a spray-dried powder. Typically, all the ingredients are mixed together by a mixing process. By way of example in such a process, the binder, for example silica, in the form of a gel is mixed with the P-zeolite and the resultant mixture is extruded into the desired shape, for example cylindic or multi-lobe bars. Spherical shapes can be made in rotating granulators or by oil-drop technique. Small spheres can further be made by spray-drying a catalyst suspension.

Thereafter, the catalyst is calcined in air or an inert gas, typically at a temperature of from 350 to 900° C. for a period of from 1 to 48 hours. Optionally the air or an inert gas may contain steam in concentration from 10 to 90 vol %.

As regards steps c) and d*), the dried or calcined, shaped catalyst particles may optionally be finished by contacting them with water or an aqueous exchange solution of an ionic compound. The aqueous exchange solution is characterized in that it is effective for removing undesired metallic cations that may occupy the ion exchange sites of the molecular sieve or/and introduction a desirable metallic cations. The undesirable metallic cations are Na, K, Fe, Zn, Cr, Mn, Ni, V, Mo, Co, Cu, Cd. These species can originate from inorganic template material present in the molecular sieve or, more commonly, stem from the inorganic oxide binder source material (e.g. aluminum sol). In the processing service for which the catalyst is designed these metal cations can promote side reactions, slow the desired reaction rate, or otherwise complicate the catalysis of the desired reaction. Some sources of the inorganic oxide binder are essentially free of undesired metal cations and therefore the dried particles produced using such sources would not necessarily require contact with an exchange solution. Water washing both before and after the finishing step may be desired to flush the catalyst of undesired solids and/or residual exchange solution.

In accordance with the present invention, at the step c) and d*) the catalyst is treated with water for a period of time advantageously from 0.5 to 48 hours, preferably for a period of time from about 1 to 36 hours and most preferably from about 2 to 24 hours. The water was at a temperature between about 10° and 180° C., preferably between about 15° and 100° C. and most preferably between about 20° and 60° C. Following the water treatment, the catalyst was dried at about 60-350° C. Optionally, the water can contain ammonium or at least one of the metallic cations ions selected from the group consisting of Li, Ag, Mg, Ca, Sr, Ba, Ce, Al, La, and mixtures thereof which do not promote side reactions and stabilize the zeolite against steam dealumination.

One skilled in the art will also appreciate that the olefins made by the dehydration process of the present invention can be, by way of example, polymerized. When the olefin is ethylene it can be, by way of example, polymerized to form polyethylenes, dimerized to butene and then isomerised to isobutene, said isobutene reacting with ethanol to produce ETBE, dimerised to 1-butene, trimerised to 1-hexene or tetramerised to 1-octene, said alpha-olefins comonomers are further reacted with ethylene to produce polyethylene dimerised to 1-butene, said 1-butene is isomerised to 2-butene and said 2-butene is further converted with ethylene by metathesis reaction into propylene and said propylene can be polymerised to polypropylene, converted to ethylene oxide and glycol or converted to vinyl chloride.

The present invention relates also to said polyethylenes, polypropylene, propylene, butane, hexane, octene, isobutene, ETBE, vinyl chloride, ethylene oxide and glycol.

EXAMPLES

The stainless-steel reactor tube has an internal diameter of 11 mm. 10 ml of catalyst, as pellets of 35-45 mesh, is loaded in the tubular reactor. The void spaces before and after the catalyst bed are filled with SiC granulates of 1 mm. The temperature profile is monitored with the aid of a thermocouple well placed inside the reactor. The reactor temperature is increased at a rate of 60° C./h to 550° C. under nitrogen, kept 1 hour at 550° C. and then purged by nitrogen. The nitrogen is then replaced by the feed at the indicated operating conditions.

Analysis of the products is performed by using an on-line gas chromatography.

Surfin 96 bio-ethanol

In the examples below, the bio-ethanol used is a Surfin 96 bio-ethanol, meaning this ethanol produced by fermentation has been submitted to different distillation and purification steps so as to get a high purity bio-ethanol.

The characteristics of the Surfin 96 bio-ethanol used in the examples below are gathered table 1.

TABLE 1

| Main characteristics of Surfin96 bio-ethanol | | | |
|---|---|---|---|
| | | | Surfin 96 |
| Tot S | | ppm | <0.2 |
| Tot N | | ppm | <0.5 |
| Basic volatile | | | |
| N | | ppm | <1 |
| Na | | mg/l | 0.5 |

TABLE 1-continued

| Main characteristics of Surfin96 bio-ethanol | | | |
|---|---|---|---|
| | | | Surfin 96 |
| Ca | | mg/l | <0.1 |
| Mn | | mg/l | <0.1 |
| Fe | | mg/l | <0.5 |
| Cu | | mg/l | <0.2 |
| Zn | | mg/l | <0.1 |
| Alcohol content | | % vol @ 20° C. | 96.1 |
| | | g/hl | |
| Total acidity | | acetic acid | 0.8 |
| Esters | | g/hl | <0.1 |
| Acetaldehyde/ Acetal | | g/hl | <0.1 |

Example 1

Catalyst A:

The catalyst is a phosphorous modified zeolite (P-ZSM5), prepared according to the following recipe. A sample of zeolite ZSM-5 (Si/Al=13) in H-form was steamed at 550° C. for 6 h in 100% $H_2O$. Then, 1270 g of the steamed solid was subjected to a contact with an aqueous solution containing 241.3 g of $H_3PO_4$ (85% wt) for 2 h under reflux condition (4 ml/1 g zeolite). Then 69.9 g of CaCO3 was introduced. Then the solution was dried by evaporation for 3 days at 80° C. 750 g of the dried sample was extruded with 401.5 g of colloidal silica (Bindzil, 34 wt % of SiO2, 200 ppm of Na) and 0.01 wt % of extrusion additives. The extruded solid was dried at 110° C. for 16 h and calcinated at 600° C. for 10 h. The catalyst was then equilibrated 2 hours at 600° C. under steam.

The sample is hereinafter identified as catalyst A.

Ethanol Dehydration Using Catalyst A

In this example, a mixture of 95% wt Surfin96 ethanol and 5% wt water have been processed on catalyst A under the following dehydration conditions: outlet pressure of 2bara, a weight hour space velocity referred to raw ethanol of 7 $h^{-1}$, downflow, inlet temperature of 400° C. FIG. 1 shows the evolution of the ethanol conversion (full points) and the ethylene yield (open points) as a function of time of stream.

TABLE 2

| Performances of the dehydration catalyst A at 400° C. under 2bara pressure using Surfin 96 bio-ethanol diluted with 5% wt water, the WHSV (ethanol) = 7 $h^{-1}$, 400° C. | |
|---|---|
| FEED | EtOH/H2O (95/5)% wt Surfin 96 |
| P (bara) | 2 |
| T (° C.) | 400 |
| WHSV (H−1) | 7 |
| EtOH conversion (% wt CH2) | 99.95 |
| DEE | 0.0 |
| Acetaldyde | 0.38 |
| Yield on C-basis (% wt CH2) | |
| CH4 | 0.0 |
| C2 | 0.21 |
| C2= | 95.6 |
| C3= | 0.9 |
| C4+ olef | 2.3 |
| C4+ paraf | 0.3 |
| Aromatics | 0.1 |
| Unknown | 0.13 |

TABLE 2-continued

Performances of the dehydration catalyst A at 400°
C. under 2bara pressure using Surfin 96 bio-ethanol diluted
with 5% wt water, the WHSV (ethanol) = 7 h$^{-1}$, 400° C.

| FEED | EtOH/H2O (95/5)% wt Surfin 96 |
|---|---|
| Selectivity on C-basis (% wt CH2) | |
| CH4 | 0.0 |
| C2 | 0.21 |
| C2= | 95.7 |
| C3= | 0.9 |
| C4+ olef | 2.3 |
| C4+ paraf | 0.3 |
| Aromatics | 0.1 |
| Unknown | 0.1 |
| C2's purity (%) | 99.79 |

Example 2

Catalyst B Synthesis:

A sample of zeolite ZSM-5 (Si/Al=12) in H-form (contained 445 ppm of Na, below 25 ppm of K, 178 ppm of Fe, 17 ppm of Ca & synthesized without template) was steamed at 550° C. for 6 h in 100% H$_2$O at atmospheric pressure. Then, 600 g of the steamed solid was subjected to a contact with an aqueous solution of H$_3$PO$_4$ for 2 h under reflux condition (114 g of H3PO4, 4 ml/1 g zeolite) followed by introduction of 35 g of CaCO3 and evaporation under stirring.

720 g of the dried sample was extruded with 121 g of SiO2 in form of Bindzil colloidal silica (34 wt % of SiO2, 200 ppm of Na) and 2 wt % of extrusion additives. The extruded solid was dried at 110° C. for 16 h, and steamed for 2 h at 600° C. in 100% steam.

The sample is hereinafter identified as catalyst B.

Ethanol to Ethylene Using Catalyst B

Figure 2:
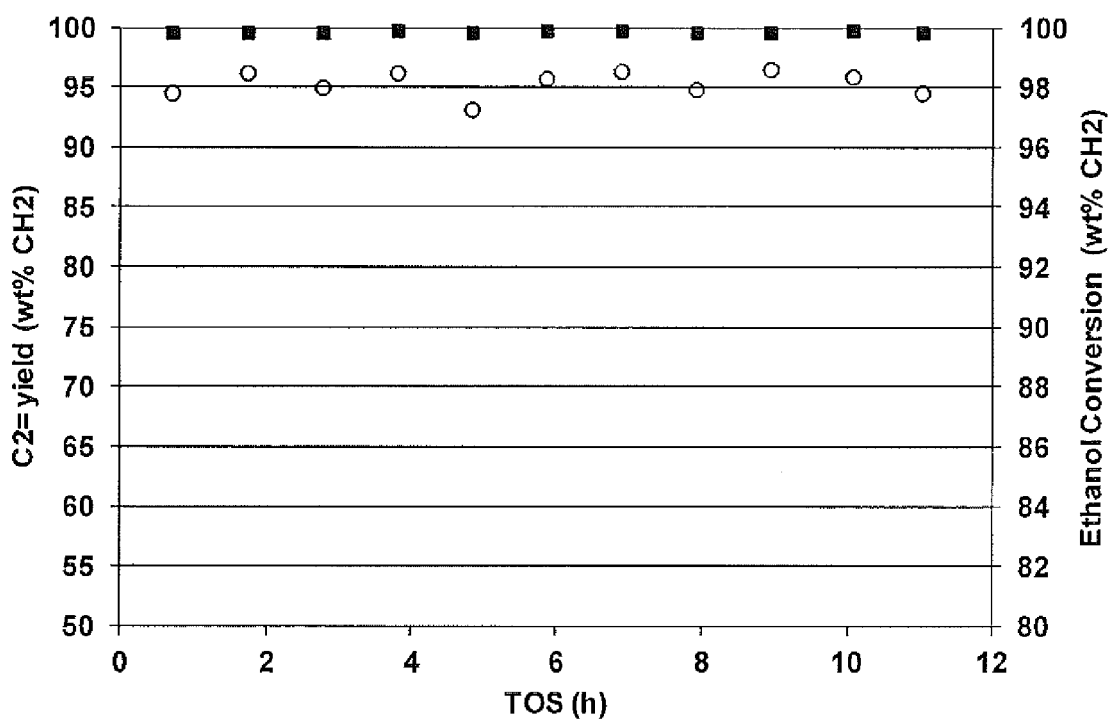
FIG. 2 shows the evolution of the ethanol conversion (full rectangles) and the ethylene yield (open circles) as a function of time of stream. Catalyst B. Surfin 96 bio-ethanol diluted with 5 wt % water—360° C.–2bara—WHSV(Ethanol): 7 h-1

In this example, a mixture of 95% wt Surfin96 ethanol and 5% wt water have been processed on catalyst B under the following dehydration conditions: outlet pressure of 2bara, a weight hour space velocity referred to raw ethanol of 7 h$^{-1}$, downflow, inlet temperature of 400° C. FIG. 2 shows the evolution of the ethanol conversion (rectangle) and the ethylene yield (lozenges) as a function of time of stream.

TABLE 3

Performances of the dehydration catalyst B at 360°
C. under 2bara pressure using Surfin 96 bio-ethanol
diluted with 5% wt water, the WHSV (ethanol) = 7 h$^{-1}$.

| FEED | EtOH/H2O (95/5)% wt |
|---|---|
| P (bara) | 2 |
| T (° C.) | 360 |
| WHSV (H–1) | 7 |
| EtOH conversion (% wt CH2) | 99.91 |
| DEE | 0.0 |
| Acetaldyde | 0.19 |
| Yield on C-basis (% wt CH2) | |
| CH4 | 0.0 |
| C2 | 0.21 |
| C2= | 95.5 |
| C3= | 0.9 |
| C4+ olef | 2.3 |
| C4+ paraf | 0.5 |
| Aromatics | 0.1 |
| Unknown | 0.18 |

TABLE 3-continued

Performances of the dehydration catalyst B at 360°
C. under 2bara pressure using Surfin 96 bio-ethanol
diluted with 5% wt water, the WHSV (ethanol) = 7 h$^{-1}$.

| FEED | EtOH/H2O (95/5)% wt |
|---|---|
| Selectivity on C-basis (% wt CH2) | |
| CH4 | 0.0 |
| C2 | 0.21 |
| C2= | 95.6 |
| C3= | 0.9 |
| C4+ olef | 2.3 |
| C4+ paraf | 0.5 |
| Aromatics | 0.1 |
| Unknown | 0.2 |
| C2's purity (%) | 99.78 |

Butanol Dehydration Using Catalyst B:

In this example, an isobutanol/water mixture having the 95/5 wt % composition has been processed on the catalyst under 1.5 bara, at temperatures of 280 and 300° C., and with an isobutanol space velocity of about 7 h$^{-1}$.

In this set of operating conditions, isobutanol conversion is almost complete, with a butenes selectivity of 90% wt or above, and an iso-butene selectivity of about 66-67%. Thus, nearly 90% or more butenes are produced, in which a significant amount are skeletal isomerised into n-butenes. The heavies production is limited to 10% or less.

TABLE 4

Performances of the dehydration catalyst B at 280°
C. and 300° under 1.5bara pressure using Surfin 96
bio-ethanol diluted with 5% wt water, the WHSV (ethanol) = 7 h$^{-1}$.

| FEED: i-ButOH/H2O (95/5)% wt | | |
|---|---|---|
| P (bara) | 1.5 | 1.5 |
| T (° C.) | 300 | 280 |
| WHSV (H–1) | 7.4 | 7.4 |
| Conversion (% wt CH2) | 100.0 | 83.5 |
| Oxygenates (% wt CH2) - Average | | |
| Other alcohols | 0.01 | 0.00 |
| Other Oxygenates | 0.03 | 0.08 |
| Selectivity on C-basis (% wt CH2) - Average | | |
| Paraffins C1-C4 | 0.1 | 0.1 |
| C2= | 0.0 | 0.0 |
| C3= | 0.5 | 0.3 |
| C4= | 89.9 | 93.9 |
| i-Butene | 60.3 | 61.9 |
| 1-Butene | 5.0 | 6.1 |
| 2-Butene | 24.6 | 26.0 |
| C5+ olef | 4.8 | 2.7 |
| C5+ paraf | 1.9 | 1.1 |
| Dienes | 0.5 | 0.4 |
| Aromatics | 0.5 | 0.2 |
| Unknown | 1.6 | 1.1 |
| C4= distribution - Average | | |
| i-Butene | 67.1 | 65.9 |
| n-butenes | 32.9 | 34.1 |
| 1-Butene | 5.5 | 6.5 |
| 2-Butene | 27.4 | 27.7 |

Example 3 (Comparative)

This example illustrates that the binder presence in the catalyst interferes with introduction of phosphorous into zeolite. The solid obtained by phosphotation of the extruded zeolite by wet impregnation using the same proportion on zeolite basis of the reagents as in case of powder (catalyst A, B), results in non-selective catalyst for dehydration.

Catalyst C synthesis (Comparative):

30 g of the sample of ZSM-5 (Si/Al=12) in NH4-form (contained 445 ppm of Na, below 25 ppm of K, 178 ppm of Fe, 17 ppm of Ca & synthesized without template) was extruded with 20 wt % of SiO2 in form of precipitated silica (contained 680 ppm of sodium) and 2 wt % of extrusion additives. Then, the extruded sample was calcined at 600° C. for 10 h and steamed at 550° C. for 6 h in 100% of H2O.

The 25 g of steamed solid was subjected to a contact with an aqueous solution containing 3.8 g of H3PO4 (4.2 ml H20/1 g zeolite) under reflux conditions during 2 h. Then 1 g of CaCO3 was introduced. The resulted solid was separated from the solution, dried at 110° C. for 16 h and equilibrated by steaming at 600° C. for 2 h.

The sample is hereinafter identified as sample C.

Ethanol to Ethylene Using Catalyst B & C for Comparison

In these examples 1 ml of catalyst, as pellets of 35-45 mesh and diluted in 9 ml of SiC 0.5 mm, is loaded in the tubular reactor. A mixture of 25% wt Surfin96 ethanol and 75% wt water have been processed on catalyst B & catalyst C in the same dehydration conditions: outlet pressure of 2bara, a weight hour space velocity referred to raw ethanol of 7 $h^{-1}$, downflow, inlet temperature of 380° C.

| FEED | Comparison | |
|---|---|---|
| | Catalyst B | Catalyst C (Comparative) |
| | | EtOH/H2O (25/75%) |
| P (bara) | 2 | 2 |
| T (° C.) | 380 | 380 |
| WHSV (H−1) | 7 | 7 |
| EtOH conversion (% wt CH2) | 99.91 | 99.97 |
| Selectivity on C-basis (% wt CH2) | | |
| C2= | 98.3 | 97.4 |
| C3= | 0.4 | 0.7 |
| C4+ olefins | 0.6 | 1.3 |
| C4+ paraffins | 0.1 | 0.3 |

The table above shows that the catalyst C produces more heavy products (C3=, C4+) and lower ethylene selectivity than the catalyst B.

What is claimed:

1. A method comprising:
converting an alcohol having at least 2 carbon atoms into a corresponding olefin in a dehydration process, wherein conversion of the alcohol is performed in the presence of a catalyst, wherein a method of making the catalyst comprises the following steps in sequential order:
a) introducing phosphorus into a zeolite comprising at least one ten member ring in a structure thereof,
b) mixing the phosphorus modified zeolite of step a) with at least a component selected among one or more binders, salts of alkali-earth metals, salts of rare-earth metals, clays and shaping additives,
b)* making a catalyst body from the mixture of step b),
c) an optional drying step or an optional drying step followed by a washing step,
d) a calcination step,
d*) an optional washing step followed by drying,
wherein all phosphorus in the zeolite is introduced in step a) prior to introduction of any binder, salt of alkali-earth metal, salt of rare-earth metal, clay or shaping additive to the zeolite.

2. The method according to claim 1 wherein an amount of phosphorous introduced into the zeolite at step a) is from 0.5 to 30 wt %.

3. The method according to claim 2 wherein the amount of phosphorous introduced into the zeolite at step a) is from 0.5 to 9 wt %.

4. The method according to claim 1 wherein the zeolite contains less than 1000 wppm of sodium, less than 1000 wppm of potassium and less than 1000 wppm of iron.

5. The method according to claim 1 wherein the zeolite contains less than 100 ppm of red-ox and noble elements.

6. The method according to claim 1 wherein alkali-earth metals and salts of rare-earth metals are Ca, Mg, Sr, Ce, La or a combination thereof.

7. The method according to claim 1 wherein the zeolite structure is selected from the MFI, MTT, FER, MEL, TON, MWW, EUO, MFS, ZSM-48.

8. The method according to claim 1 wherein the proportion of the phosphorus modified zeolite is from 15 to 90 wt % of the catalyst.

9. The method according to claim 1 wherein a concentration of the salts of alkali-earth metals is from 0.1 to 15 wt % of the catalyst on metal basis (Me).

10. The method according to claim 1 wherein a molar ratio of (Al+Me)/P in the catalyst is in the range 0.5 to 3, where the Me is alkali or rare-earth, P is phosphorus, and Al is aluminum.

11. The method according to claim 1 wherein the zeolite contains less than 100 ppm of Zn, Cr, Ti, Rh, Mn, Ni, V, Mo, Co, Cu, Cd, Pt, Pd, Ir, Ru, or Re.

12. The method according to claim 1 wherein a concentration of the salts of rare-earth metals is from 0.1 to 15 wt % of the catalyst on metal basis (Me).

13. The method according to claim 1 wherein a P/Al ratio in step a) is higher than 1, wherein P is phosphorus and Al is aluminum.

14. The method according to claim 1, wherein the washings in step c) and step d*) are performed and comprise treating the catalyst with water for a period of time ranging from 0.5 to 48 hours, wherein the water is at a temperature between about 10° C. and 180° C., and wherein the dryings in step c) and step d*) are performed and comprise drying the catalyst at a temperature of about 60° C. to 350° C.

15. The method according to claim 14, wherein the water contains:
ammonium;
at least one ions selected from the group consisting of Li, Ag, Mg, Ca, Sr, Ba, Ce, Al, La, and mixtures thereof; or combinations thereof.

16. The method according to claim 1 wherein, prior to introduction of the phosphorus into the zeolite, the zeolite is:
steamed at a temperature ranging from 480 to 760° C. and then leached.

17. The method according to claim 1 wherein the zeolite has a silicon to aluminum ratio, prior to introduction of the phosphorus, that is below 20.

18. A method for making a catalyst comprising the following steps in this order:
a) introducing phosphorus into a zeolite comprising at least one ten member ring in a structure thereof,
b) mixing the phosphorus modified zeolite of step a) with at least a component selected among one or more binders, salts of alkali-earth metals, salts of rare-earth metals, clays and shaping additives,
b)* making a catalyst body from the mixture of step b),
c) an optional drying step or an optional drying step followed by a washing step, d) a calcination step, d*) an optional washing step followed by drying, wherein all phosphorus in the zeolite is introduced in step a), and wherein the zeolite has a silicon to aluminum ratio, prior to introduction of the phosphorus, that is below 20.

19. The method according to claim 18 wherein all of the phosphorus is introduced into the zeolite prior to introduction of any binder, salt of alkali-earth metal, salt of rare-earth metal, clay or shaping additive to the zeolite.

20. A method comprising:

introducing phosphorus into a zeolite comprising at least one ten member ring in a structure thereof to form a phosphorus modified zeolite, wherein the zeolite has a silicon to aluminum ratio, prior to introduction of the phosphorus, that is below 20, and wherein the zeolite structure is selected from MFI, MTT, FER, MEL, TON, MWW, EUO, MFS, and ZSM-48;

mixing the phosphorus modified zeolite with at least a component selected among one or more binders, salts of alkali-earth metals, salts of rare-earth metals, clays and shaping additives to form a mixture;

making a catalyst body from the mixture;

calcining the catalyst body to form a catalyst; and converting an alcohol having at least 2 carbon atoms into a corresponding olefin in a dehydration process, wherein conversion of the alcohol is performed in the presence of the catalyst;

wherein all phosphorus in the zeolite is introduced prior to introduction of any binder, salt of alkali-earth metal, salt of rare-earth metal, clay or shaping additive to the zeolite.

* * * * *